United States Patent [19]

Araki

[11] Patent Number: 4,473,890

[45] Date of Patent: Sep. 25, 1984

[54] METHOD AND DEVICE FOR STORING STEREOCHEMICAL INFORMATION ABOUT CHEMICAL COMPOUNDS

[75] Inventor: Keisuke Araki, Hasuda, Japan

[73] Assignee: The Japan Information Center of Science & Technology, Tokyo, Japan

[21] Appl. No.: 422,921

[22] Filed: Sep. 24, 1982

[30] Foreign Application Priority Data

Apr. 7, 1982 [JP] Japan .................................. 57-56750

[51] Int. Cl.³ ............................................ G06F 15/20
[52] U.S. Cl. ................................................. 364/900
[58] Field of Search ......................... 364/900 MS File

[56] References Cited

U.S. PATENT DOCUMENTS 4,085,443 4/1978 Dubois et al. ....................... 364/900

Primary Examiner—Raulfe B. Zache
Attorney, Agent, or Firm—Sughrue, Mion, Zinn, Macpeak, and Seas

[57] ABSTRACT

The structure of a compound is expressed as an atom connection table using an electronic computer. The structure is registered in a three-dimensional manner, making it possible to effect the interconversion between the atom connection table and symbols R, S that represent absolute configuration of asymmetric carbon atoms, or $\alpha$, $\beta$ that represent directions of substitution relative to the plane the ring. Namely, in the case of a ring compound, bonded atoms in the clockwise and counterclockwise directions, and bonded atoms in the upward and downward directions of the ring are stored in the separate predetermined registers. In the case of a chain compound, bonded atoms in the right and left directions, and bonded atoms in the upward and downward directions are stored in the separate predetermined registers. On the atom connection table, therefore, the rotational directing of bonded atoms can be defined as viewed from a given direction. It is therefore possible to prepare the atom connection table reflecting the symbols in the compound name, to store three-dimensional structures of compounds, and to process and produce the data.

4 Claims, 5 Drawing Figures

METHOD AND DEVICE FOR STORING STEREOCHEMICAL INFORMATION ABOUT CHEMICAL COMPOUNDS

BACKGROUND OF THE INVENTION

1. Field of the Invention

The present invention relates to a method and device for storing stereochemical information about chemical compounds.

2. Prior Art

Chemical compounds have three-dimensional structures by their own nature. When information about these compounds is to be stored in electronic computers, however, various difficulties are encountered since it has to be expressed two-dimensionally. In particular, it is difficult to discriminate compounds which, when rotated in space, afford sterically different structures as well as to identify the compounds which must be stereochemically the same.

A method has, therefore, been employed to describe all of the three-dimensional coordinates of the atoms and to store them. With such a method however, the storage capacity must be tremendously great, involving much redundancy, and the three-dimensional agreements are not necessarily guaranteed.

There has also been proposed a chemical compound registry system by Chemical Abstracts Service in U.S.A., in which only stereodescriptors are involved. With this method, however, the descriptors have no correspondence with each atom in the connection table; i.e., the method cannot meet the requirement of the increasing complicated information related to the stereochemistry. With this method, furthermore, it is difficult to concretely describe which atom is arranged and in what manner. Moreover, with regard to compounds of formulas III and IV that will be mentioned later, the stereodescriptors are different, i.e., (2R, 4S) for III and (2S, 4R) for IV, so that the compounds may be regarded as completely different from each other. To avoid such misjudgement, the structures of the compounds must be checked and corrected manually.

SUMMARY OF THE INVENTION

The object of the present invention is to provide a method and device for storing stereochemical information about chemical compounds, according to which the stereochemical information can be correctly described in an atom connection table and can be corresponded to the stereodescriptors on an atomic level.

DESCRIPTION OF THE PREFERRED EMBODIMENTS

Figure 1:
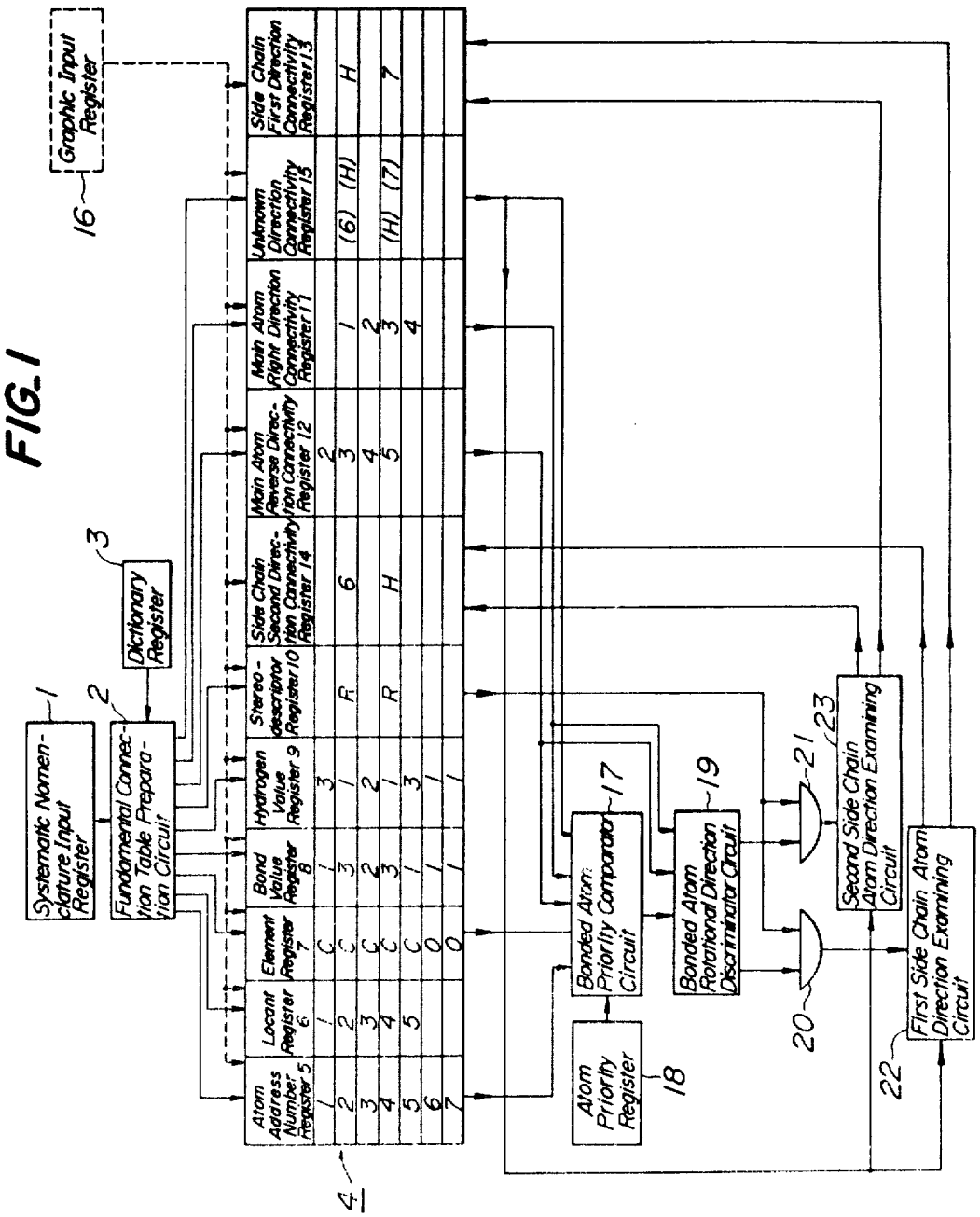
FIGS. 1, 3 and 4 are block diagrams of a memory device according to three embodiments of the present invention.

The invention will now be described concretely referring to its embodiments.

2,4-Pentanediol is a chain compound consisting of three stereoisomers that can be described as formulas I, II and III on a paper according to Fischer's projection method which describes the main chain in the upward and downward directions. An isomer of formula IV is obtained by turning the isomer of formula III by 180° on the plane of paper.

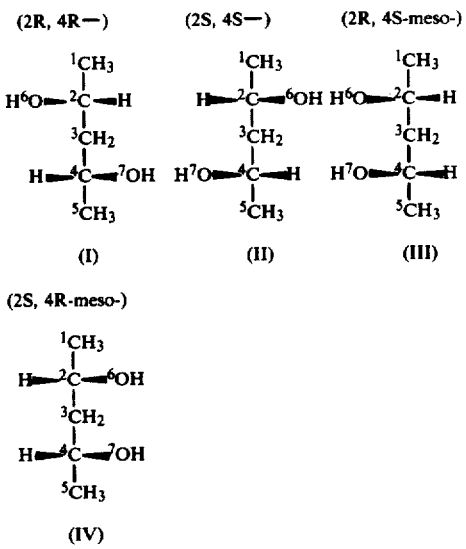

In these formulas, a solid line "—" represents a bond laid on a plane of the paper, and a symbol "■" represents one that protrudes upward from the plane of the paper. Formula I refers to (2R, 4R)-2,4-pentanediol, formula II to (2S, 4S)-2,4-pentanediol, formula III to (2R, 4S)-meso-2,4-pentanediol, and formula IV to (2S, 4R)-meso-2,4-pentanediol. The numerals attached to the atoms except the hydrogen atom H are atom address numbers which are arbitrarily assigned to specify and store the atoms.

The isomers of formulas I, II and III cannot be superposed on each other no matter how they are turned. The isomers of formulas III and IV, on the contrary, are identical.

In order to distinguish and store the above-mentioned relations according to the present invention, use is made of a main atom right direction connectivity register as means for specifying and storing connectivity in the right direction of main atoms which form a skeleton of the compound (in a chain compound in which the main chain is described to array in the upward and downward directions according to Fischer's projection method, the upward direction is referred to as right direction and, in a ring compound, the clockwise direction is referred to as right direction), and use is made of a main atom reverse direction connectivity register as means for specifying and storing connectivity in the reverse direction of main atoms which form a skeleton of the compound (in the chain compound, the downward direction is referred to as reverse direction and, in the ring compound, the counterclockwise direction is referred to as reverse direction). Further, connectivities are stored to correspond to atom address numbers of the atoms by using a side chain first direction connectivity register as means for specifying and storing connectivities of side chain atoms bonded to the main atoms in the first direction (in a chain compound, the right front direction is referred to as the first direction and, in a ring compound, the direction which protrudes upward from the plane of the paper is referred to as the first direction), and by using a side chain second direction connectivity register as means for specifying and storing connectivities of side chain atoms bonded to the main atoms in the second direction (in the chain compound, the left front direction is referred to as the second direction and, in the ring compound, the direction which protrudes downward from the plane of the paper is referred to as the second direction).

In a chain compound described according to Fischer's projection method, when the main chain is laterally described because of its length or by some other reasons, the direction from the right to the left is referred to as the right direction, the direction from the left to the right is referred to as the reverse direction, the upper front direction is referred to as the first direction, and the lower front direction is referred to as the second direction.

By using the above-mentioned registers, the atoms in the compound described by Fischer's projection method can be stored in a three-dimensional manner. By using such registers, furthermore, the data stored in the main atom right direction connectivity register and those stored in the main atom reverse direction connectivity register can be exchanged for each storage field of the same atom address number, and the data stored in the side chain first direction connectivity register and those stored in the side chain second direction connectivity register can be exchanged for each storage field of the same atom address number, such that the stored data can be changed, for instance, from formula III into formula IV, or vice versa, making it possible to easily compare whether the isomer of formula III is identical with one of formula IV.

Concerning assignment of address numbers to atoms of a compound, a unique numbering method, i.e., Morgan's numbering rule is available which is proposed by J. P. Morgan of the U.S.A. By storing atom numbers as determined by Morgan's numbering rule, stereoisomers can be discriminated and identified very easily, or the data related to the stereochemistry of compounds can be retrieved very easily.

Hereinafter follows the description for storing formulas I, II, III and IV with reference to Tables I, II, III and IV.

Formula I in which the atom address numbers are arbitrarily assigned to the atoms, can be numbered as shown by formulas I-$M_{01}$ and I-$M_{02}$ according to Morgan's numbering rule.

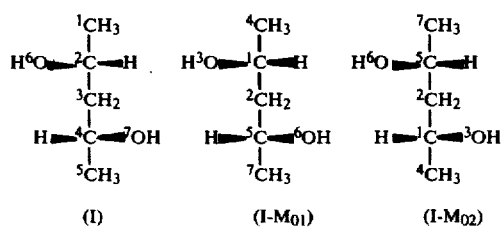

(I)         (I-$M_{01}$)         (I-$M_{02}$)

The atoms of formulas I, I-$M_{01}$ and I-$M_{02}$ correspond to the address numbers by the method of the present invention, and are stored in the registers as shown in Table I.

TABLE I

| Form-ula | Atom address number register | Locant re-gister | Ele-ment re-gister | Bond value re-gister | Hydro-gen value re-gister | Stereo-descriptor |
|---|---|---|---|---|---|---|
| I | 1 | 1 | C | 1 | 3 | |
| | 2 | 2 | C | 3 | 1 | R |
| | 3 | 3 | C | 2 | 2 | |
| | 4 | 4 | C | 3 | 1 | R |
| | 5 | 5 | C | 1 | 3 | |
| | 6 | | O | 1 | 1 | |
| | 7 | | O | 1 | 1 | |
| I-$M_{01}$ | 1 | 2 | C | 3 | 1 | R |
| | 2 | 3 | C | 2 | 2 | |
| | 3 | | O | 1 | 1 | |
| | 4 | 1 | C | 1 | 3 | |
| | 5 | 4 | C | 3 | 1 | R |
| | 6 | | O | 1 | 1 | |
| | 7 | 5 | C | 1 | 3 | |
| I-$M_{02}$ | 1 | 4 | C | 3 | 1 | R |
| | 2 | 3 | C | 2 | 2 | |
| | 3 | | O | 1 | 1 | |
| | 4 | 5 | C | 1 | 3 | |
| | 5 | 2 | C | 3 | 1 | R |
| | 6 | | O | 1 | 1 | |
| | 7 | 1 | C | 1 | 3 | |

| Side chain second direction connectivity register | Main atom reverse direction connectivity register | Main atom right direction connectivity register | Side chain first direction connectivity register |
|---|---|---|---|
| | 2 | | |
| 6 | 3 | 1 | H |
| | 4 | 2 | |
| H | 5 | 3 | 7 |
| | | 4 | |
| 3 | 2 | 4 | H |
| | 5 | 1 | |
| | 1 | | |
| H | 7 | 2 | 6 |
| | | 5 | |
| H | 4 | 2 | 3 |
| | 1 | 5 | |
| | | 1 | |
| 6 | 2 | 7 | H |
| | 5 | | |

Formula I can be stored in a following manner.

Atom address numbers 1 to 7 assigned to the atoms of formula I except the hydrogen atom, are stored in the atom address number register.

The locant register stores the locants that specify, from the chemical point of view, the positions of the atoms that constitute the main chain of formula I, to correspond to the atom address numbers.

The element register stores the kinds of atoms to which the atom address numbers are assigned, in a manner of C, C, C, C, C, O, O so as to correspond to the atom address numbers 1, 2, 3, 4, 5, 6 and 7 of the atoms.

The bond value register stores bond values of the atoms to which the atom address numbers are assigned, and which are bonded to the atoms other than the hydrogen atoms, so as to correspond to the atom address numbers of the atoms. For instance, in the case of a carbon atom C having atom address number 1, the bond value to the atom other than the hydrogen atom is 1. In the case of a carbon atom C having atom address number 2, the bond value to the atom other than the hydrogen atom is 3. The bond values of other atoms are determined in the same nammer, and are stored to correspond to the atom address numbers.

The hydrogen value register stores the number of hydrogen atoms connected to the atoms to which the atom address numbers are assigned, to correspond to the atom address numbers of the atoms. For instance, in the case of the carbon atom C having atom address number 1, the bond number relative to the hydrogen atoms is 3, and in the case of the carbon atom C having atom address number 2, the bond number relative to the hydrogen atoms is 1. The bond numbers of other atoms are determined in the same manner as above even, and are stored to correspond to the atom address numbers.

The stereodescriptor register stores stereodescriptors R (Rectus: which means right in Latin), and S (Sinister: which means left) assigned to asymmetric carbon atoms with atom address numbers 2 and 4, to correspond to the atom address number 2 and 4.

The main atom right direction connectivity register stores which main atom is bonded in the right direction (an upward direction in the case of a chain compound) to a main atom of the main chain which constitutes the skeleton of the compound, i.e., stores the atom address number of the bonded main atom in a place corresponding to the atom address number of the bonding main atom. In this example, no main atom which constitutes the main chain is bonded from above to the carbon atom C of atom address number 1. Therefore, the main atom right direction connectivity register stores nothing in a place which corresponds to the atom address number 1. The carbon atom C having atom address number 1 is bonded from above to the carbon atom C having atom address number 2. Therefore, the main atom right direction connectivity register stores 1 in a portion corresponding to the atom address number 2. The same holds with other main atoms.

The main atom reverse direction connectivity register stores which main atom is bonded in the reverse direction (a downward direction in the case of a chain compound) to a main atom of the main chain which constitutes the skeleton of the compound, i.e., stores the atom address number of the bonded main atom in a place corresponding to the atom address number of the bonding main atom. In this example, carbon atom C of the atom address number 2 is bonded from below to the carbon atom C of atom address number 1. Therefore, the main atom reverse direction connectivity register stores 2 in a location which corresponds to the atom address number 1. Further, since the carbon atom C with atom address number 3 is bonded from below to the carbon atom C with atom address number 2, the main atom reverse direction connectivity register stores 3 in a place corresponding to the atom address number 2. The same holds with other main atoms.

The side chain first direction connectivity register stores the atom address numbers or the atomic symbols of bonded side-chain atoms in the locations corresponding to the atom address numbers of the atoms of the main chain to which the side-chain atoms are bonded in the first direction (a right front direction in the case of a chain compound). In this example, a hydrogen atom H is bonded in the first direction, i.e., in the right front direction of the carbon atom C with atom address number 2. Therefore, H is stored in the side chain first direction connectivity register in a location corresponding to the atom address number 2. Further, an oxygen atom O of atom address number 7 is bonded in the first direction, i.e., in the right front direction of the carbon atom C with atom address number 4. Therefore, the side chain first direction connectivity register stores 7 in a location corresponding to the atom address number 4.

The side chain second direction connectivity register stores the atom address numbers or the atomic symbols of bonded side-chain atoms in the locations corresponding to the atom address numbers of the atoms of the main chain to which the side-chain atoms are bonded in the second direction (a left front direction in the case of the chain compound). In this example, an oxygen atom O of atom address number 6 is bonded in the second direction, i.e., in the left front direction of carbon atom C with atom address number 2. Therefore, the side chain second direction connectivity register stores 6 in a location corresponding to the atom address number 2. Further, a hydrogen atom H is bonded in the second direction, i.e., in the left front direction of carbon atom C of atom address number 4. Therefore, the side chain second direction connectivity register stores H in a location which corresponds to the atom address number 4.

Formulas I-$M_{01}$ and I-$M_{02}$ are stored as follows. Namely, the atom address number register stores atom address numbers which are assigned to the atoms, except hydrogen atoms, of formulas I-$M_{01}$ and I-$M_{02}$ according to Morgan's numbering rule. The data for other registers are stored in the same manner as in the case of formula I. In this case, the atom address numbers stored in the registers are those assigned according to Morgan's numbering rule.

Similarly, formulas II, III and IV in which the address numbers are arbitrarily assigned to the atoms, can be expressed as formulas II-$M_{01}$, II-$M_{02}$, III-$M_{01}$, III-$M_{02}$ and IV-$M_{01}$, according to Morgan's numbering rule. Further, formula IV-R is obtained by turning formula IV-$M_{01}$ by 180° on the plane of paper.

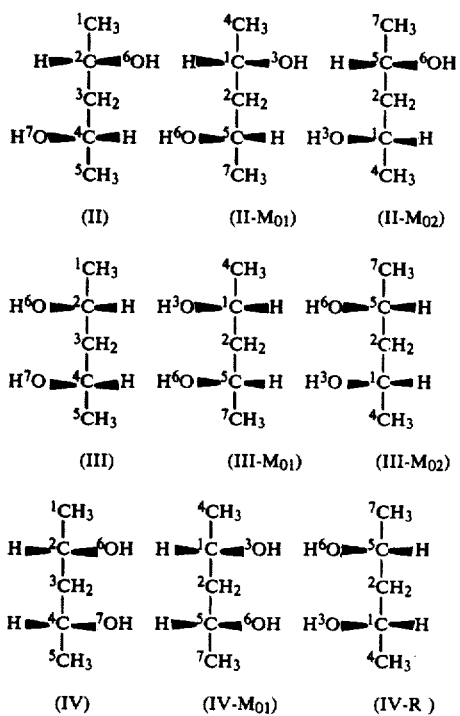

The atoms of these formulas II, II-$M_{01}$, II-$M_{02}$, III, III-$M_{01}$, III-$M_{02}$, IV, IV-$M_{01}$ and IV-R are stored in the registers to correspond to the address numbers, as illustrated in Tables II, III and IV.

TABLE II

| Formula | Atom address number register | Locant register | Element register | Bond value register | Hydrogen value register | Stereodescriptor register |
| --- | --- | --- | --- | --- | --- | --- |

TABLE II-continued

| Formula | Atom address number register | Locant register | Element register | Bond value register | Hydrogen value register | Stereo-descriptor register |
|---|---|---|---|---|---|---|
| II | 1 | 1 | C | 1 | 3 | D |
|  | 2 | 2 | C | 3 | 1 | S |
|  | 3 | 3 | C | 2 | 2 |  |
|  | 4 | 4 | C | 3 | 1 | S |
|  | 5 | 5 | C | 1 | 3 |  |
|  | 6 |  | O | 1 | 1 |  |
|  | 7 |  | O | 1 | 1 |  |
| II $M_{01}$ | 1 | 2 | C | 3 | 1 | S |
|  | 2 | 3 | C | 2 | 2 |  |
|  | 3 |  | O | 1 | 1 |  |
|  | 4 | 1 | C | 1 | 3 |  |
|  | 5 | 4 | C | 3 | 1 | S |
|  | 6 |  | O | 1 | 1 |  |
|  | 7 | 5 | C | 1 | 3 |  |
| II $M_{02}$ | 1 | 4 | C | 3 | 1 | S |
|  | 2 | 3 | C | 2 | 2 |  |
|  | 3 |  | O | 1 | 1 |  |
|  | 4 | 5 | C | 1 | 3 |  |
|  | 5 | 2 | C | 3 | 1 | S |
|  | 6 |  | O | 1 | 1 |  |
|  | 7 | 1 | C | 1 | 3 |  |

| Side chain Second direction connectivity register | Main atom reverse direction connectivity register | Main atom right direction connectivity register | Side chain first direction connectivity register |
|---|---|---|---|
|  | 2 |  |  |
| H | 3 | 1 | 6 |
|  | 4 | 2 |  |
| 7 | 5 | 3 | H |
|  |  | 4 |  |
| H | 2 | 4 | 3 |
|  | 5 | 1 |  |
|  | 1 |  |  |
| 6 | 7 | 2 | H |
|  |  | 5 |  |
| 3 | 4 | 2 | H |
|  | 1 | 5 |  |
|  |  | 1 |  |
| H | 2 | 7 | 6 |
|  | 5 |  |  |

TABLE III

| Formula | Atom address number register | Locant register | Element register | Bond value register | Hydrogen value register | Stereo-descriptor register |
|---|---|---|---|---|---|---|
| III | 1 | 1 | C | 1 | 3 |  |
|  | 2 | 2 | C | 3 | 1 | R |
|  | 3 | 3 | C | 2 | 2 |  |
|  | 4 | 4 | C | 3 | 1 | S |
|  | 5 | 5 | C | 1 | 3 |  |
|  | 6 |  | O | 1 | 1 |  |
|  | 7 |  | O | 1 | 1 |  |
| III $M_{01}$ | 1 | 2 | C | 3 | 1 | R |
|  | 2 | 3 | C | 2 | 2 |  |
|  | 3 |  | O | 1 | 1 |  |
|  | 4 | 1 | C | 1 | 3 |  |
|  | 5 | 4 | C | 3 | 1 | S |
|  | 6 |  | O | 1 | 1 |  |
|  | 7 | 5 | C | 1 | 3 | S |
| III $M_{02}$ | 1 | 4 | C | 3 | 1 | S |
|  | 2 | 3 | C | 2 | 2 |  |
|  | 3 |  | O | 1 | 1 |  |
|  | 4 | 5 | C | 1 | 3 |  |
|  | 5 | 2 | C | 3 | 1 | R |
|  | 6 |  | O | 1 | 1 |  |
|  | 7 | 1 | C | 1 | 3 |  |

| Side chain second direction connectivity register | Main atom reverse direction connectivity register | Main atom right direction connectivity register | Side chain first direction connectivity register |
|---|---|---|---|
|  | 2 |  |  |
| 6 | 3 | 1 | H |
|  | 4 | 2 |  |
| 7 | 5 | 3 | H |
|  |  | 4 |  |
| 3 | 2 | 4 | H |
|  | 5 | 1 |  |
|  | 1 |  |  |
| 6 | 7 | 2 | H |
|  |  | 5 |  |
| 3 | 4 | 2 | H |
|  | 1 | 5 |  |
|  |  | 1 |  |
| 6 | 2 | 7 | H |
|  | 5 |  |  |

TABLE IV

| Formula | Atom address number register | Locant register | Element register | Bond value register | Hydrogen value register | Stereo-descriptor register |
|---|---|---|---|---|---|---|
| IV | 1 | 1 | C | 1 | 3 |  |
|  | 2 | 2 | C | 3 | 1 | S |
|  | 3 | 3 | C | 2 | 2 |  |
|  | 4 | 4 | C | 3 | 1 | R |
|  | 5 | 5 | C | 1 | 3 |  |
|  | 6 |  | O | 1 | 1 |  |
|  | 7 |  | O | 1 | 1 |  |
| IV $M_{01}$ | 1 | 2 | C | 3 | 1 | S |
|  | 2 | 3 | C | 2 | 2 |  |
|  | 3 |  | O | 1 | 1 |  |
|  | 4 | 1 | C | 1 | 3 |  |
|  | 5 | 4 | C | 3 | 1 | R |
|  | 6 |  | O | 1 | 1 |  |
|  | 7 | 5 | C | 1 | 3 |  |
| IV $M_{02}$ | 1 | 4 | C | 3 | 1 | S |
|  | 2 | 3 | C | 2 | 2 |  |
|  | 3 |  | O | 1 | 1 |  |
|  | 4 | 5 | C | 1 | 3 |  |
|  | 5 | 2 | C | 3 | 1 | R |
|  | 6 |  | O | 1 | 1 |  |
|  | 7 | 1 | C | 1 | 3 |  |

| Side chain second direction connectivity register | Main atom reverse direction connectivity register | Main atom right direction connectivity register | Side chain first direction connectivity register |
|---|---|---|---|
|  | 2 |  |  |
| H | 3 | 1 | 6 |
|  | 4 | 2 |  |
| H | 5 | 3 | 7 |
|  |  | 4 |  |
| H | 2 | 4 | 3 |
|  | 5 | 1 |  |
|  | 1 |  |  |
| H | 7 | 2 | 6 |
|  |  | 5 |  |
| 3 | 4 | 2 | H |
|  | 1 | 5 |  |
|  |  | 1 |  |
| 6 | 2 | 7 | H |
|  | 5 |  |  |

In the atom connection tables I, II, III and IV thus obtained, the direction from the atom stored in a given column of the main atom right direction connectivity register to the one stored in the same column of the main atom reverse direction connectivity register, assumes a clockwise turn when the formulas are seen from the right.

Further, among the individual register of the atom connection tables I, II, III and IV, if the data stored in the main atom right direction connectivity register and those stored in the main atom reverse direction connectivity register are exchanged for each of the atom address numbers, and the data stored in the side chain first direction connectivity register and those stored in the de chain second direction connectivity register are exchanged for each of the atom address numbers, the result is the same as that obtained by turning the formulas of a chain compound by 180° on the plane of paper. Thus, formula III-$M_{02}$ comes into perfect agreement with formula IV-R which is obtained by turning formula IV-$M_{01}$ by 180° on the plane of paper, though formulas I, I-$M_{01}$, I-$M_{02}$, II, II-$M_{01}$, II-$M_{02}$, III, III-$M_{01}$ and III-$M_{02}$ afford different formulas when they are turned.

Incidentally, in a chain compound expressed by Fischer's projection method, turning the formula upside down on the plane of paper is meaningless.

Isomers of formulas I, II and III which cannot be distinguished in an ordinary planar atom connection table, can, according to the method of the present invention, be stereochemically distinguished. It can be also recognized that the isomer of formula III is identical with the one of formula IV.

Memory device for storing stereochemical information about a chain compound will now be described with reference to the case of (2R, 4R)-2,4-pentanediol. As shown in FIG. 1, the device is equipped with a systematic nomenclature input register 1 which introduces the systematic nomenclature of a compound as character data. Output of the register 1 is suppled to a fundamental connection table preparation circuit 2 which prepares a fundamental connection table based upon the data from a dictionary register 3 which stores a variety of data. Output of the circuit 2 is stored in the predetermined registers of a fundamental connection table register 4 which is equipped with an atom address number register 5, a locant register 6, an element register 7, a bond value register 8, a hydrogen value register 9, a stereodescriptor register 10, a main atom right direction connectivity register 11, a main atom reverse direction connectivity register 12, a side chain first direction connectivity register 13, a side chain second direction connectivity register 14, and an unknown direction connectivity register 15. The input to the fundamental connection table register 4 may be obtained from a graphic input register 16. In this case, the data from the graphic input register 16 can be stored in all of the registers in the fundamental connection table register 4, except the stereodescriptor register 10.

The following circuit is provided to store in the registers 13 and 14 the data on the three-dimensional bonding state of side-chain atoms bonded to asymmetric atoms that cannot be input via the fundamental connection table preparation circuit 2. First, provision is made of a bonded atom priority comparator circuit 17 which compares the priority of atoms bonded to assymetric atoms based upon signals from the registers 5, 7, 11, 12 and 15 in the fundamental connection table register 4 and upon the date from an atom priority register 18 which stores priority in weight of the atoms bonded to the asymmetric atoms. The comparator circuit 17 compares and determines the priority in weight of the atoms bonded to the asymmetric atoms.

The output signal from the comparator circuit 17 is supplied to a bonded atom rotational direction discriminator circuit 19 which discriminates the rotational direction of the atoms bonded to the asymmetric atoms. The discriminator circuit 19 discriminates whether the rotational direction from heavy atoms to light atoms based upon the priority in weight of the atoms bonded to the asymmetric atoms, is in agreement with the rotational direction of atoms as viewed from the direction of the register 11 to the register 12 in the fundamental connection table register 4.

A coincidence signal produced by the discriminator circuit 19 is supplied to a first AND circuit 20 which works as a first stereodescriptor reading circuit. A non-coincidence signal produced by the discriminator circuit 19 is supplied to a second AND circuit 21 that works as a second stereodescriptor reading circuit. The first AND circuit 20 receives another input from the stereodescriptor register 10, and reads the stereodescriptor data R or S sent from the stereodescriptor register 10 when the coincidence signal is applied thereto from the discriminator circuit 19. The second AND circuit 21 receives another input from the stereodescriptor register 10, and reads the stereodescriptor data R or S from the stereodescriptor register 10, when the non-coincidence signal is applied thereto from the discriminator circuit 19.

Figure 2:
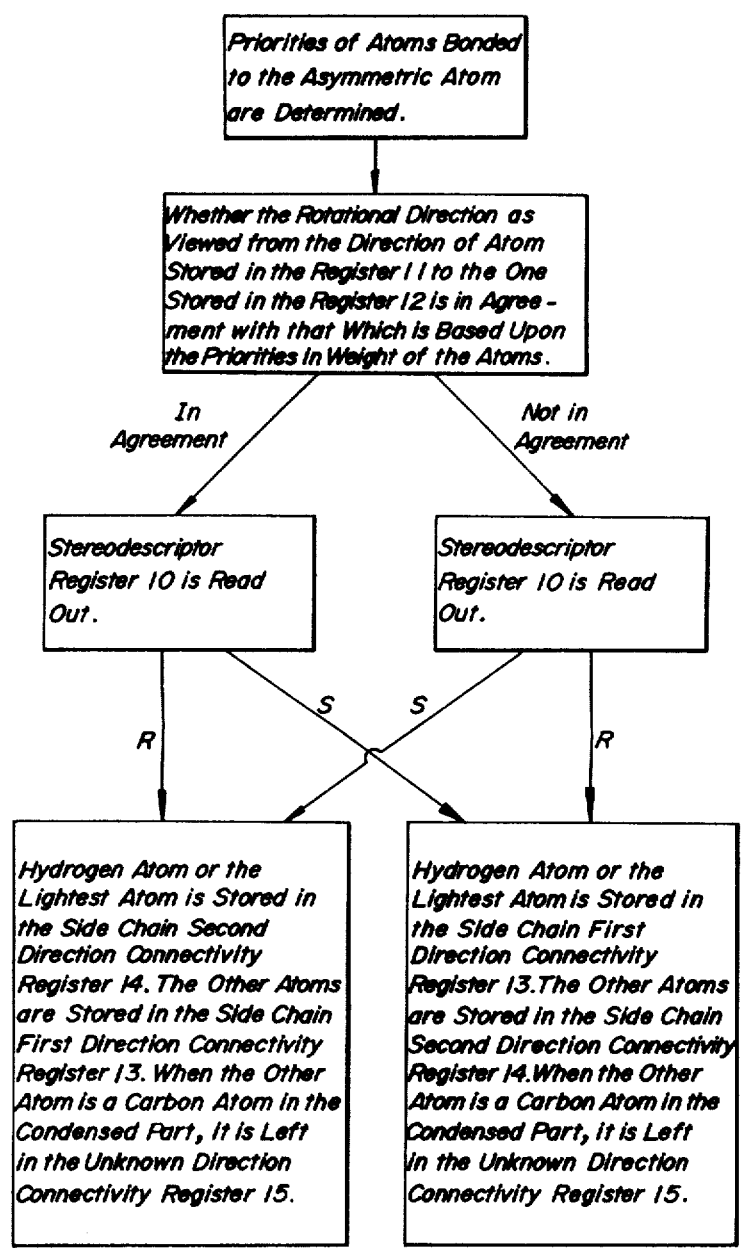
FIG. 2 is a flow chart for discriminating the portions to be stored in the device of FIGS. 1 and 3.

Output of the first AND circuit 20 which has read the stereodescriptor register 10 upon receipt of the coincidence signal, is supplied to a first side chain atom direction examining circuit 22 which, when the stereodescriptor data R is read from the first AND circuit 20, stores the hydrogen atom H or the lightest atom between the two atoms temporarily stored in the unknown direction connectivity register 15 in the field of a predetermined atom address number of the side chain second direction connectivity register 14, and stores the other atom temporarily stored in the unknown direction connectivity register 15 in the field of a predetermined atom address number of the side chain first direction connectivity register 13, as illustrated in a flow chart of FIG. 2. When the stereodescriptor data S is read from the first AND circuit 20, furthermore, the examining circuit 22 stores the hydrogen atom H or the lightest atom between the two atoms temporarily stored in the unknown direction connectivity register 15 in the field of a predetermined atom address number of the side chain first direction connectivity register 13, and stores the other atom temporarily stored in the unknown direction connectivity register 15 in the field of a predetermined atom address number of the side chain second direction connectivity register 14.

The output of the second AND circuit 21 which has read the stereodescriptor register 10 upon receipt of the non-coincidence signal, is applied to a second side chain atom direction examining circuit 23 which, when the stereodescriptor data R is read from the second AND circuit 21, stores the hydrogen atom H or the lightest atom between the two atoms temporarily stored in the unknown direction connectivity register 15 in the field of a predetermined atom address number of the side chain first direction connectivity register 13, and stores the other atom temporarily stored in the unknown direction connectivity register 15 in the field of a predetermined atom address number of the side chain second direction connectivity register 14, as illustrated in the flow chart of FIG. 2. When the stereodescriptor data S is read from the second AND circuit 21, furthermore, the examining circuit 23 stores the hydrogen atom H or the lightest atom between the two atoms temporarily stored in the unknown direction connectivity register 15 in the field of a predetermined atom address number of the side chain second direction connectivity register 14, and stores the other atom temporarily stored in the unknown direction connectivity register 15 in the field of a predetermined atom address number of the side chain first direction connectivity register 13.

In the device thus constructed, a systematic nomenclature such as (2R, 4R)-2,4-pentanediol expressed by the formula I, which is input to the input register 1, is converted into predetermined electric signals which are then input to the fundamental connection table preparation circuit 2 which breaks down the introduced data, i.e., (2R, 4R)-2,4-pentanediol into, for instance, "2R, 4R", "2, 4", "pentane", and "diol", such that the individual data as stored in the registers 5, 6, 7, 8, 9, 10, 11, 12 and 15 of the fundamental connection table register 4, to correspond to the atom address numbers relying upon the data from the dictionary register 3, as illustrated above in conjunction with Table I. Provision of the unknown direction connectivity register 15 makes the fundamental connection table register 4 different from Table I. The unknown direction connectivity register 15 temporarily stores the side-chain atoms of which the directions of bonding to the asymmetric atoms are difficult to determine. In this embodiment, the unknown direction connectivity register 15 stores 6 and H for the atom address number 2, and stores H and 7 for the atom address number 4.

When the data are stored in the registers of the fundamental connection table register 4, the data in the registers 5, 7, 11, 12 and 15 related to asymmetric atoms of the atom address numbers 2 and 4, are successively supplied to the bonded atom priority comparator circuit 17 for every asymmetric atoms with the atom address numbers 2, 4.

Upon receipt of signals from the registers 11, 12 and 15, the comparator circuit 17 detects that the asymmetric carbon atom C with atom address number 2 possesses a hydrogen atom H, $CH_3$ having a carbon atom C with atom address number 1, $CH_2$ having a carbon atom C with atom address number 3, and OH having an oxygen atom O with atom address number 6, that are connected thereto. Priorities in weight of these atoms, except hydrogen atoms H, are compared based upon the data from the atom priority register 18. In this case, the weight of atoms decreases in the order of oxygen atom O with atom address number 6, carbon atom C with atom address number 3, and carbon atom C with atom address number 1. The priority in weight is determined in the following way:

Based upon signals produced by the bonded atom priority comparator circuit 17, the bonded atom rotational direction discriminator circuit 19 discriminates whether the rotational direction from the heavy atom toward the light atom based upon the priority in weight of the atoms bonded to the asymmetric carbon atom C with atom address number 2, is in agreement with the clockwise rotational direction as viewed from the register 11 to the register 12 of the fundamental connection table register 4. For easy comprehension of the priority in weight of the atoms bonded to the asymmetric carbon atom C with atom address number 2, the priority order is indicated by encircled figures in the following formula I-A.

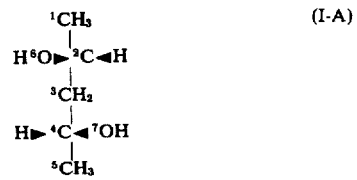

It will be understood that the rotational direction of the atoms bonded to the asymmetric carbon atom C with atom address number 2 based upon the priority of weight is 6→3→1 as viewed from the right side of the formula I-A. In this case, the direction from the carbon atom C with atom address number 1 stored in the field of atom address number 2 in the register 11 to the carbon atom C with atom address number 3 stored in the register 12 is 1→3, which is a clockwise turn, and which does not agree with the above-mentioned rotational direction 6→3→1. Therefore, the rotational direction 6→3→1 is a counterclockwise rotation. The above discrimination is effected by the bonded atom rotational direction discriminator circuit 19. The non-coincidence signal produced from the discriminator circuit 19 is supplied to the second AND circuit 21 which works as a second stereodescriptor reading circuit which reads the data R stored in the stereodescriptor register 10 in the field of atom address number 2. The stereodescriptor data R which is read out, is supplied to a second side chain atom direction examining circuit 23. Upon receipt of the stereodescriptor data R, the second side chain atom direction examining circuit 23 works to store the hydrogen atom H temporarily stored in the unknown direction connectivity register 15 in the field of atom address number 2 of the side chain first direction connectivity register 13 and works to store the oxygen atom O of atom address number 6 temporarily stored in the unknown direction connectivity register 15 in the field of atom address number 2 of the side chain second direction connectivity register 14, as illustrated in the flow chart of FIG. 2. That is, when the stereodescriptor data is R, and the rotational direction is not in agreement, the hydrogen atom H is placed in front of the carbon atom C with atom address number 2 as viewed from the right side of the formula I-A.

Then, upon receipt of signals from the registers 11, 12 and 15, the comparator circuit 17 detects that the asymmetric carbon atom C with atom address number 4 possesses a hydrogen atom H, $CH_2$ having a carbon atom C with atom address number 3, $CH_3$ having a carbon atom C with atom address number 4, and OH having an oxygen atom O with atom address number 7, which are connected thereto. Priorities in weight of the atoms except hydrogen atoms H, are compared based upon the data from the atom priority register 18. In this case, priority in weight of the atoms decreases in the order of oxygen atom O with atom address number 7, carbon atom C with atom address number 3, and carbon atom C with atom address number 5.

Based upon the signals produced by the bonded atom priority comparator circuit 17, the bonded atom rotational direction discriminator circuit 19 discriminates whether the rotational direction of the atoms bonded to the asymmetric carbon atom C of atom address number 4 based upon the priority in weight is in agreement with the clockwise rotational direction as viewed in the direction of from the register 11 to the register 12 of the fundamental connection table register 4. For easy comprehension of the priority in weight of the atoms bonded to the asymmetric carbon atom C of atom address number 4, the priority order is indicated by encircled figures in the following formula I-B.

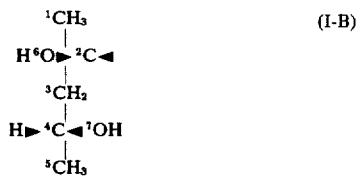

It will be understood that the rotational direction of the atoms bonded to the asymmetric carbon atom C with atom address number 4 based upon the priority of weight is 7→3→5, as viewed from the right side of the formula I-B. In this case, the direction from the carbon atom C with atom address number 3 stored in the field of atom address number 4 in the register 11 to the carbon atom C with atom address number 5 stored in the register 12 is 3→5, which is a clockwise turn, and which is in agreement with the rotational direction 7→3→5. The above discrimination is effected by the bonded atom rotational direction discriminator circuit 19. The coincidence signal produced from the discriminator circuit 19 is supplied to the first AND circuit 20 which works as a first stereodescriptor reading circuit which reads the data R stored in the stereodescriptor register 10 in the field of atom address number 4. The stereodescriptor data R which is read out, is supplied to the first side chain atom direction examining circuit 22. Upon receipt of the stereodescriptor data R, the first side chain atom direction examining circuit 22 works to store the hydrogen atom temporarily stored in the unknown direction connectivity register 15 in the field of atom address number 4 of the side chain second direction connectivity register 14, and works to store the oxygen atom O of atom address number 7 temporarily stored in the unknown direction connectivity register 15 in the field of atom address number 4 of the side chain first direction connectivity register 13, as illustrated in the flow chart of FIG. 2. That is, when the stereodescriptor data is R, and the rotational directions are in agreement, the hydrogen atom H is placed at the back of the carbon atom C with atom address number 4 as viewed from the right side of the formula I-B.

Formulas I-$M_{01}$ and I-$M_{02}$ are stored as follows. Namely, atom address numbers of formula I are converted into atom address numbers of formulas I-$M_{01}$ and I-$M_{02}$, and are automatically stored in the device.

Formulas II, II-$M_{01}$, II-$M_{02}$ to IV, IV-$M_{01}$ and IV-R are also stored in the same manner.

Below is described how to store a ring compound in the three-dimensional manner. According to Fischer's projection method, (3S)-cholestan-3-ol can be expressed by formula V, in which atom address numbers are arbitrarily assigned to the atoms except hydrogen atoms. In this formula, broken lines represent bonds that protrude downward from the plane of the paper.

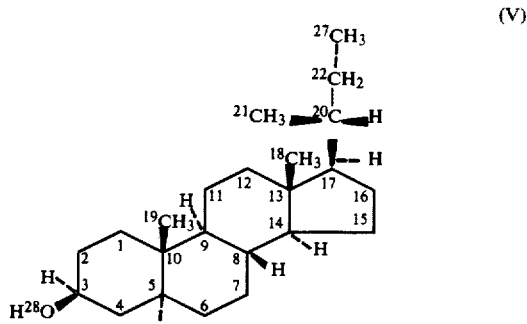

In this case, the numbers are assigned to the ring atoms in a conventional manner.

The atoms of formula V, according to the method of the present invention, are stored in the registers to correspond to the address numbers, as illustrated in Table V.

TABLE V

| Formula | Atom address number register | Locant register | Element register | Bond value register | Hydrogen value register | Condensation register | Stereodescriptor register |
|---|---|---|---|---|---|---|---|
| V | 1 | 1 | C | 2 | 2 | | |
| | 2 | 2 | C | 2 | 2 | | |
| | 3 | 3 | C | 3 | 1 | | S |
| | 4 | 4 | C | 2 | 2 | | |
| | 5 | 5 | C | 3 | 1 | J | S |
| | 6 | 6 | C | 2 | 2 | | |
| | 7 | 7 | C | 2 | 2 | | |
| | 8 | 8 | C | 3 | 1 | J | R |
| | 9 | 9 | C | 3 | 1 | J | S |
| | 10 | 10 | C | 4 | 0 | J | S |
| | 11 | 11 | C | 2 | 2 | | |
| | 12 | 12 | C | 2 | 2 | | |
| | 13 | 13 | C | 4 | 0 | J | R |
| | 14 | 14 | C | 3 | 1 | J | R |
| | 15 | 15 | C | 2 | 2 | | |
| | 16 | 16 | C | 2 | 2 | | |
| | 17 | 17 | C | 3 | 1 | | R |
| | 18 | 18 | C | 1 | 3 | | |
| | 19 | 19 | C | 1 | 3 | | |
| | 20 | 20 | C | 3 | 1 | | |
| | 21 | 21 | C | 1 | 3 | | |
| | 22 | 22 | C | 2 | 2 | | |
| | 23 | 23 | C | 2 | 2 | | |
| | 24 | 24 | C | 2 | 2 | | |
| | 25 | 25 | C | 3 | 1 | | |
| | 26 | 26 | C | 1 | 3 | | |

TABLE V-continued

| | | | | |
|---|---|---|---|---|
| 27 | 27 | C | 1 | 3 |
| 28 | 28 |   | 0 |   |

| Side chain second direction connectivity register | Main atom reverse direction connectivity register | Main atom right direction connectivity register | Unknown direction connectivity register | Side chain first direction connectivity register |
|---|---|---|---|---|
|   | 2  | 10 |    |    |
|   | 3  | 1  |    |    |
| H | 4  | 2  |    | 28 |
|   | 5  | 3  |    |    |
| H | 6  | 4  | 10 |    |
|   | 7  | 5  |    |    |
|   | 8  | 6  |    |    |
|   | 14 | 7  | 9  | H  |
| H | 10 | 11 | 8  |    |
|   | 1  | 9  | 5  | 19 |
|   | 9  | 12 |    |    |
|   | 11 | 13 |    |    |
|   | 12 | 17 | 14 | 18 |
| H | 15 | 8  | 13 |    |
|   | 16 | 14 |    |    |
|   | 17 | 15 |    |    |
| H | 13 | 16 |    | 20 |
|   | 13 |    |    |    |
|   | 10 |    |    |    |
|   | 17 | 22 |    | H  |
|   |    | 20 |    |    |
|   | 20 | 23 |    |    |
|   | 22 | 24 |    |    |
|   | 23 | 25 |    |    |
|   | 24 | 26 | 27 |    |
|   | 25 |    |    |    |

The data are stored as follows. Namely, the data are stored in the atom address number register, locant register, element register, bond value register, hydrogen value register, and stereodescriptor register, in the same manner as mentioned earlier.

A condensation register stores condensation symbol J which corresponds to atom address numbers of carbon atoms that form a condensed part.

The main atom right direction connectivity register stores which main atoms are bonded in the right direction (in a ring compound, the clockwise direction about the periphery of the ring is referred to as right direction) to the main atoms which form a skeleton of the ring compound, i.e., stores atom address numbers of the bonded main atoms in the places corresponding to the bonding main atom address numbers. In this example, a carbon atom C of atom address number 10 is bonded to the right of the carbon atom C of atom address number 1. Therefore, the main atom right direction connectivity register stores 10 in a location corresponding to atom address number 1. The same holds with other main atoms.

The main atom reverse direction connectivity register stores which main atoms are bonded in the reverse direction (in a ring compound, the counterclockwise direction about the periphery of the ring is referred to as reverse direction) to the main atoms forming a skeleton of the ring compound, i.e., stores atom address numbers of the bonded main atoms in the locations corresponding to atom address numbers of the bonding main atoms. In this example, a carbon atom C of atom address number 2 is bonded to the left of the carbon atom C of atom address number 1. Therefore, the main atom reverse direction connectivity register stores 2 in a location that corresponds to the atom address number 1. The same holds with other main atoms.

The side chain first direction connectivity register stores atom address numbers or atomic symbols of bonded side-chain atoms in the locations corresponding to the atom address numbers of main atoms of the ring to which the side-chain atoms are bonded in the first direction (in a ring compound, the direction protruding upward from the plane of the paper is referred to as the first direction). In this example, no atoms are bonded to the carbon atom C of atom address number 1 in the direction protruding upward from the plane of the paper. Therefore, the side chain first direction connectivity register stores nothing in a location corresponding to the atom address number 1. The carbon atom C of atom address number 3 has an oxygen atom O of atom address number 28 bonded thereto in a direction protruding upward from the plane of the paper. Therefore, the side chain first direction connectivity register stores 28 in a location corresponding to the atom address number 3. The same holds with other main atoms.

The side chain second direction connectivity register stores atom address numbers or atom symbols of bonded side-chain atoms in the locations corresponding to atom address numbers of main atoms of the ring to which the side-chain atoms are bonded in the second direction (in a ring compound, the direction which protrudes downward from the plane of the paper is referred to as the second direction). In this example, a hydrogen atom H is bonded to the carbon atom C of atom address number 3 in the direction protruding downward from the plane of the paper. Therefore, the side chain second direction connectivity register stores H in a location corresponding to atom address number 3. The same holds with other main atoms.

When it has not been determined in which one of the side chain first direction connectivity register and the side chain second direction connectivity register the side-chain atoms should be stored, the unknown direction connectivity register stores atom address numbers or atomic symbols of the side-chain atoms to correond to atom address numbers of the main atoms. The unknown direction connectivity register further stores atom address number of a carbon atom of the opposite side corresponding to a carbon atom of one side in a condensed part of the ring, in a manner to correspond to the atom address number of the carbon atom of the one side. In this example, a carbon atom of atom address number 10 is condensed with a carbon atom C of atom address number 5. Therefore, the unknown direction connectivity register stores 10 in a location corresponding to the atom address number 5. The same holds with other side-chain atoms or condensed atoms.

In the atom connection Table V thus obtained, the direction from the atom stored in a given filed of the main atom right direction connectivity register to the atom stored in the same filed of the main atom reverse direction connectivity register, is clockwise. This also means counterclockwise rotation in a condensed part of the ring.

Further, among the registers in the atom connection Table V, if the data stored in the main atom right direction connectivity register and those stored in the main atom reverse direction connectivity register are exchanged for each of the atom address numbers, and the data stored in the side chain first direction connectivity register and those stored in the side chain second direction connectivity register are exchanged for each of the atom address numbers, the result is the same as that obtained by turning formula V of the ring compound backside front.

Incidentally, in the ring compound, turning formula V by 120° in the plane of paper is meaningless.

Figure 3:
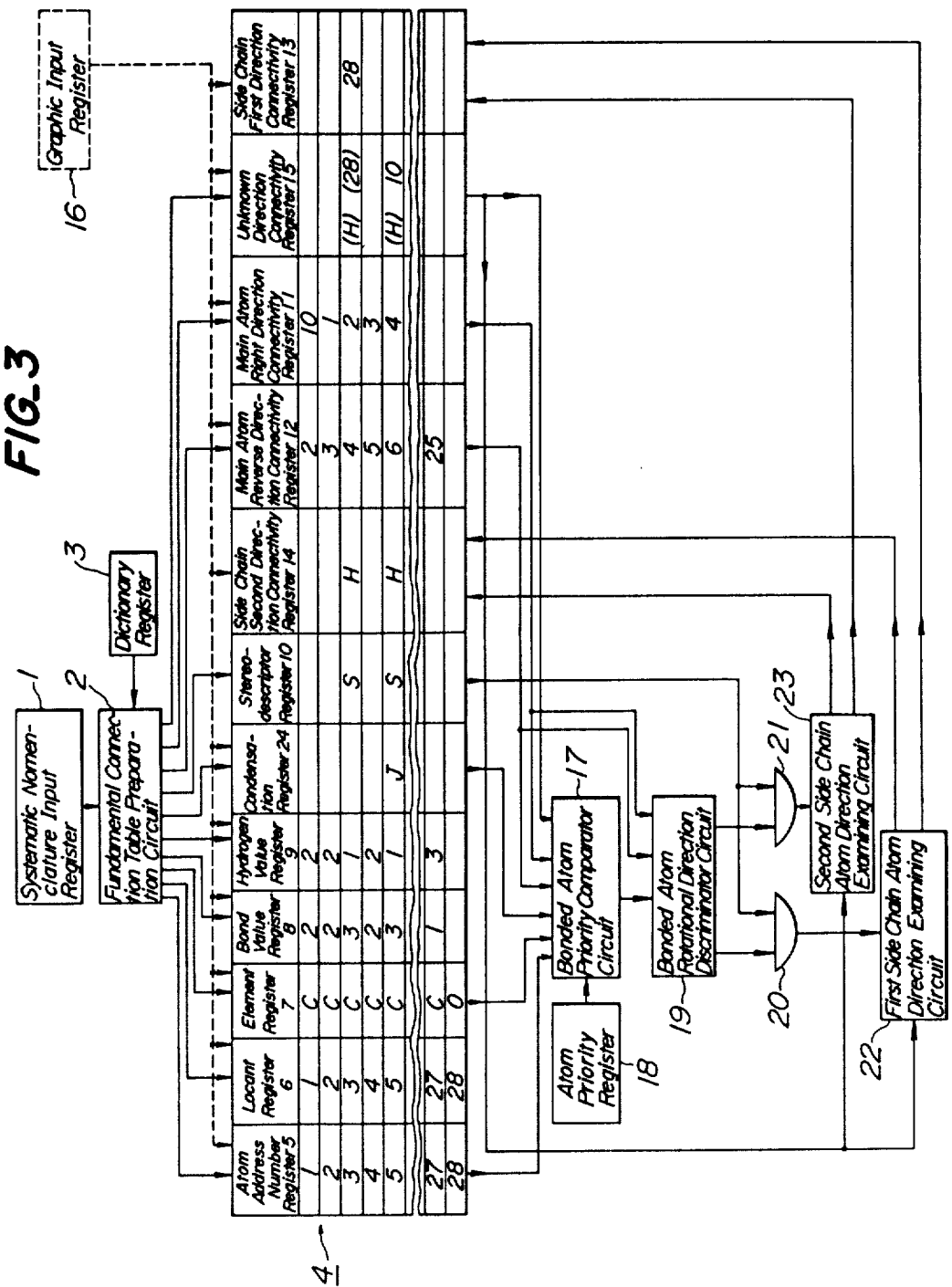

A memory device for storing stereochemical information about a ring compound will now be described with reference to the case of (3S)-cholestan-3-ol. As shown in FIG. 3, this device is nearly the same as that of FIG. 1, except that a condensation register 24 is added to the fundamental connection table register 4.

In the device thus contructed, a systematic nomenclature such as (3S)-cholestan-3-ol which is input to the input register 1, is converted into predetermined electric signals which are then input to the fundamental connection table preparation circuit 2 which breaks down the data, i.e., (3S)-choloestan-3-ol into, for instance "3S", "cholestan", "3" and "ol", such that the individual data are stored in the registers 5, 6, 7, 8, 9, 24, 10, 11, 12 and 15 of the fundamental connection table register 4, to correspond to the atom address numbers based upon the data from the dictionary register 3, as illustrated above in conjunction with Table V.

When the data are stored in the predetermined registers of the fundamental connection table register 4, the data in the registers 5, 7, 11, 12 and 15 related to asymmetric atom of the atom address numbers 3, 5, 8, 9, 10, 13, 14, 17 and 20, are successively supplied to the bonded atom priority comparator circuit 17 for every atom address number of the asymmetric atom.

Upon receipt of signals from the registers 11, 12 and 15, the comparator circuit 17 detects that the asymmetric carbon atom C of atom address number 3 has a hydrogen atom H, a carbon atom C of atom address number 2, a carbon atom C of atom address number 4, and an oxygen atom O of atom address number 28, that are connected thereto. Priorities in weight of these atoms, except hydrogen atoms H are compared based upon the data from the atom priority register 18. In this case, priorities in weight of the atom decreases in the order of oxygen atom O with atom address number 28, carbon atom C with atom address number 4, and carbon atom C with atom address number 2.

The priority in weight is determined in the following way:

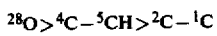

Based upon the signals produced by the bonded atom priority comparator circuit 17, the bonded atom rotational direction discriminator circuit 19 discriminates whether the rotational direction 28→4→2→28 based upon the priority in weight of the atoms bonded to the asymmetric carbon atom C of atom address number 3, is in agreement with the clockwise rotational direction 2→4 as viewed from the register 11 to the register 12 of the fundamental connection table register 4. In this case, it will be understood that the rotational direction given by the fundamental connection table register is not in agreement with the one based upon the priority in weight. The above discrimination is effected by the bonded atom rotational direction discriminator circuit 19. The non-coincidence signal produced by the discriminator circuit 19 is supplied to the second AND circuit 21 which works as a second stereodescriptor reading circuit which reads the data S stored in the stereodescriptor register 10 in the field of atom address number 3. The stereodescriptor data S which is read out, is supplied to the second side chain atom direction examining circuit 23. Upon receipt of the stereodescriptor data S, the second side chain atom direction examining circuit 23 works to store the hydrogen atom H temporarily stored in the unknown direction connectivity register 15 in the field of atom address number 3 of the side chain second direction connectivity register 14, and works to store the oxygen atom O of atom address number 28 temporarily stored in the unknown direction connectivity register 15 in the field of atom address number 3 of the side chain first direction connectivity register 13, as illustrated in the flow chart of FIG. 2. That is, when the stereodescriptor data is S, and the rotational directions are not in agreement, the hydrogen atom H is placed at the back (back side of the paper) of the carbon atom C with atom address number 3 as viewed from the front of formula V.

Then, upon receipt of signals from the registers 11, 12, 15 and 24, the comparator circuit 17 detects that the carbon atom C with atom address number 5 possesses a hydrogen atom H, carbon atom C with atom address number 4, carbon atom with atom address number 6, and carbon atom C of a condensed part with atom address number 10, which are connected thereto. Priorities in weight of the atoms except hydrogen atoms, are compared based upon the data from the atom priority register 18. In this case, priority in weight of the atoms decreases in the order of carbon atom C with atom address number 4, carbon atom C with atom address number 10, and carbon atom C with atom address number 6.

Based upon the signals produced by the bonded atom priority comparator circuit 17, the bonded atom rotational direction discriminator circuit 19 discriminates whether the rotational direction 4→10→6→4 of the atoms bonded to the asymmetric carbon atom C in a condensed part with atom address number 5 based upon the priority in weight is in agreement with the counterclockwise rotational direction 4→6 (the rotational direction is reversed in the condensed part) as viewed in the direction of from the register 11 to the register 12 of the fundamental connection table register 4. In this case, the rotational directions are not in agreement. The non-coincidence signal produced from the discriminator circuit 19 is supplied to the second AND circuit 21 which works as a second stereodescriptor reading circuit which reads the data S stored in the stereodescriptor register 10 in the field of atom address number 5. Upon receipt of the stereodescriptor data S, the second side chain atom direction examining circuit 23 works to store the hydrogen atom H temporarily stored in the unknown direction connectivity register 15 in the field of atom address number 5 of the side chain second direction connectivity register 14, and works to store the carbon atom C in the condensed part with atom address number 10 temporarily stored in the unknown direction connectivity register 15 in the same unknown direction connectivity register, as illustrated in the flow chart of FIG. 2. That is, when the stereodescriptor data is S, and the rotational directions are not in agreement, the hydrogen atom H is placed at the back (back side of the paper) of the carbon atom C with atom address number 5 as viewed from the front of the formula V.

When the (3S)-cholestan-3-ol is input as cholestan-3β-ol (β means that a side-chain atom is bonded in the direction protruding upward from the plane of the paper or, in this systematic nomenclature, ol (OH) is bonded to the atom of atom address number 3 in the front direction of the paper), the oxygen atom O with atom address number 28 bonded to the carbon atom C with atom address number 3 may, first, be stored in the side chain first direction connectivity register 13.

When the data are input from the graphic input register 16, the circuits 17, 18, 19, 20, 21, 22, 23 and 24 may be used for checking the data stored in the registers 13 and 14 of the fundamental connection table register 4.

Figure 4:
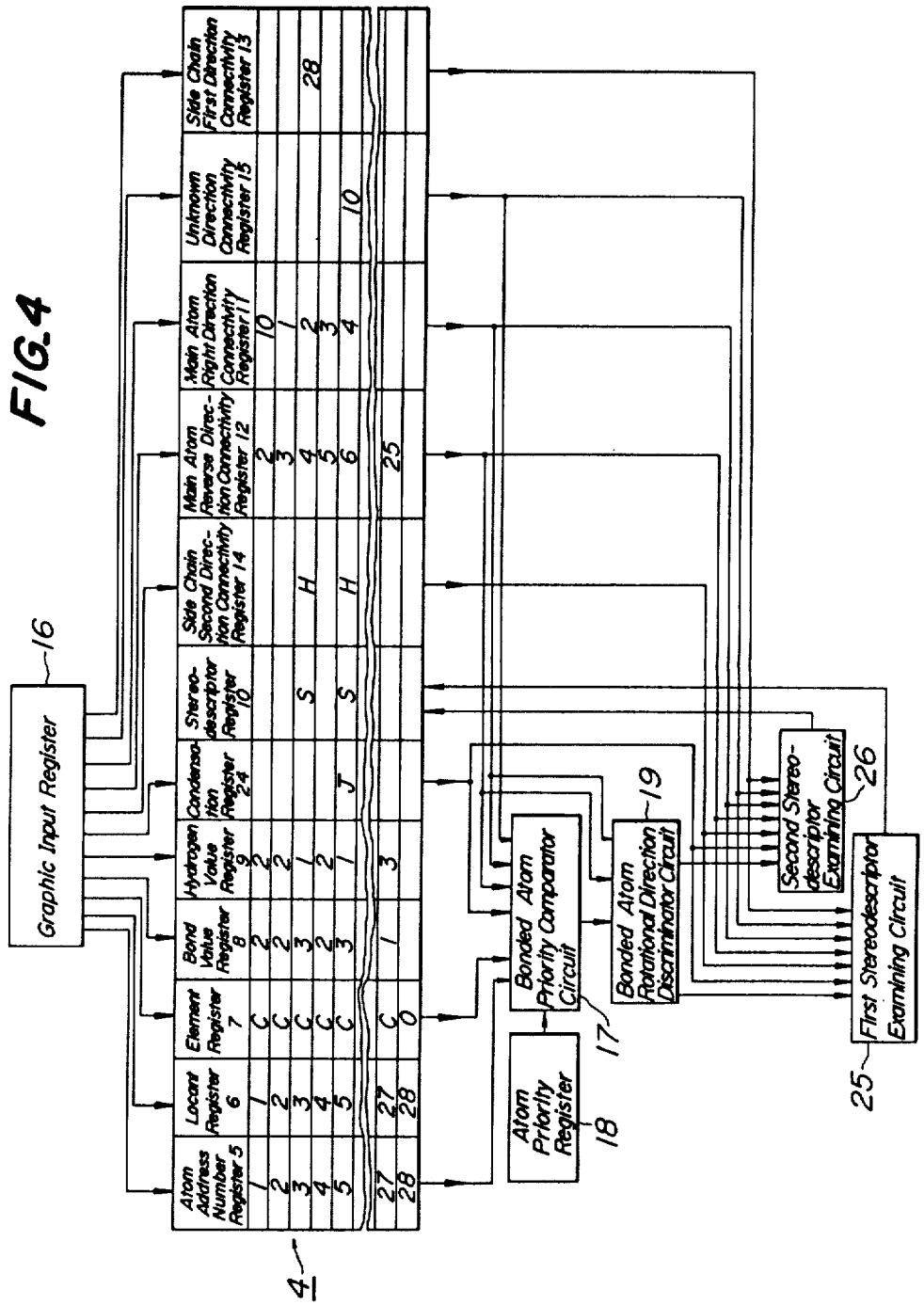

Now, the concrete setup of a memory device when the data are to be input from the graphic input register 16 to the fundamental connection table register 4 will be described by referring to FIG. 4. By using the graphic input register 16, the required data from the graphic input register 16 can be stored in the registers 5, 6, 7, 8, 9, 11, 12, 13, 14, 15 and 24 in the fundamental connection table register 4, except the stereodescriptor register 10. In the device of FIG. 4, provision is made of a first stereodescriptor examining circuit 25 and a second stereodescriptor examining circuit 26 subsequent to the bonded atom rotational direction discriminator circuit 19, in order to send stereodescriptor data that cannot be input from the graphic input register 16, to the stereodescriptor register 10.

The bonded atom rotational direction discriminator circuit 19 works to supply the coincidence signal to the first stereodescriptor examining circuit 25, and supply the non-coincidence signal to the second stereodescriptor examining circuit 26.

Figure 5:
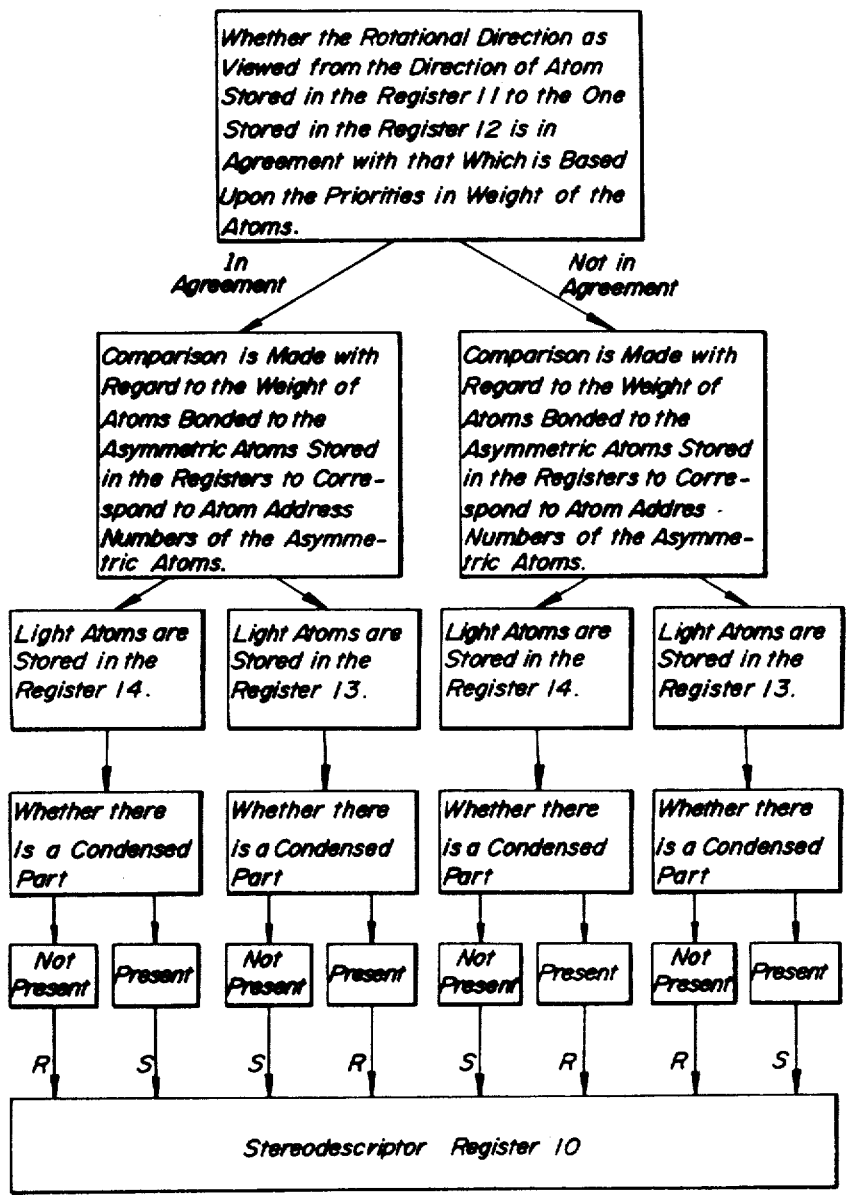
FIG. 5 is a flow chart for discriminating stereodescriptors to be stored on the stereodescriptor register in the device of FIG. 4.

Upon receipt of a signal which indicates that the rotational directions are in agreement concerning the atoms bonded to a given asymmetric atom with a given atom address number, the signal being supplied from the bonded atom rotational direction discriminator circuit 19, the first stereodescriptor examining circuit 25 compares the weight of the atoms which are bonded to the asymmetric atom and stored in the registers 11, 12, 13, 14 and 15 to correspond to the atom address number of the asymmetric atom, as illustrated in a flow chart of FIG. 5. In this case, when light atoms are stored in the regsiter 14 that stores atoms protruding toward the back side of the paper, and when the asymmetric atom does not exist in the condensed part, the stereodescriptor R is stored in the stereodescriptor registor 10 to correspond to the address number of the asymmetric atom. When the asymmetric atom exists in the condensed part, the stereodescriptor S is stored in the stereodescriptor register 10 to correspond to the address number of the asymmetric atom. Further, when light atoms are stored in the regsiter 13 that stores atoms protruding toward the front side of the paper, and when the asymmetric atom does not exist in the condensed part, the stereodescriptor S is stored in the stereodescriptor register 10 to correspond to the address number of the asymmetric atom. When the asymmetric atom exists in the condensed part, the stereodescriptor R is stored in the stereodescriptor register 10 to correspond to the address number of the asymmetric atom.

Upon receipt of a signal which indicates that the rotational directions are in agreement concerning the atoms bonded to a given asymmetric atom with a given atom address number, the signal being supplied from the bonded atom rotational direction discriminator circuit 19, the second stereodescriptor examining circuit 26 compares the weight of the atoms which are bonded to the asymmetric atom and stored in the registers 11, 12, 13, 14 and 15 to correspond to the atom address number of the asymmetric atom, as illustrated in a flow chart of FIG. 5. In this case, when light atoms are stored in the register 14 that stores atoms protruding toward the back side of the paper, and when the asymmetric atom does not exist in the condensed part, the stereodescriptor S is stored in the stereodescriptor register 10 to correspond to the address number of the asymmetric atom. When the asymmetric atom exists in the condensed part, the stereodescriptor R is stored in the stereodescriptor register 10 to correspond to the address number of the asymmetric atom. Further, when light atoms are stored in the register 13 that stores atoms protruding toward the front side of the paper, and when the asymmetric atom does not exist in the condensed part, the stereodescriptor R is stored in the stereodescriptor register 10 to correspond to the address number of the asymmetric atom. When the asymmetric atom exists in the condensed moiety, the stereodescriptor S is stored in the stereodescriptor register 10 to correspond to the address number of the asymmetric atom.

Described hereinafter is how to store the stereodescriptors using the above-mentioned device with reference to the case of graphic input of (3S)-cholestan-3-ol of formula V. When the bonded atom rotational direction discriminator circuit 19 produces a signal which indicates that the clockwise rotational direction as viewed from the register 11 to the register 12 of the fundamental connection table register is not in agreement with the rotational direction based upon the priorities in weight, concerning the atoms bonded to the asymmetric carbon atom C of atom address number 3 which is present at a place not in a condensed part, the second stereodescriptor examining circuit 26 compares the weight of the atoms stored in the registers 11, 12, 13, 14 and 15 which store the atoms bonded to the asymmetric atom in the field of atom address number 3. In this case, the lightest atom, i.e., a hydrogen atom H bonded to the asymmetric atom has been stored in the side chain second direction connectivity register 14, and the asymmetric carbon atom C of atom address number 3 does not exist in the condensed part. Therefore, the second stereodescriptor examining circuit 26 stores the stereodescriptor S in the stereodescriptor register 10 to correspond to the atom address number 3 of the asymmetric carbon atom C, as explained in the flow chart of FIG. 5. The stereodescriptor S is in agreement with a symbol 3S of the original compound.

When the bonded atom rotational direction discriminator circuit 19 produces a signal which indicates that the counterclockwise rotational direction as viewed from the register 11 to the register 12 of the fundamental connection table register 4 is in agreement with the rotational direction based upon the priorities in weight, concerning the asymmetric carbon atom of atom address number 5 present in a condensed part, the first stereodescriptor examining circuit 25 compares the weight of the atoms stored in the registers 11, 12, 13, 14 and 15 which store the atoms bonded to the asymmetric atom in the field of atom address number 5. In this case, the lightest atom, i.e., a hydrogen atom H bonded to the asymmetric atom has been stored in the side chain second direction connectivity register 14, and the asymmetric carbon atom C of atom address number 5 exists in the condensed part. Therefore, the first stereoedescriptor examining circuit 25 stores the stereodescriptor S in the stereodescriptor register 10 to correspond to the atom address number 5 of the asymmetric carbon atom C, as explained in the flow chart of FIG. 5. Discrimination is also effected for other asymmetric carbon atoms in accordance with the flow chart of FIG. 5, and the stereodescriptors are stored in the stereodescriptor register 10 to correspond to atom address numbers of the asymmetric carbon atoms.

The memory device of the present invention can be put into practice easily by using an electronic computer.

According to the method and device for storing stereochemical information about chemical compounds of the present invention, as mentioned above, use is made of a main atom right direction connectivity register, a main atom reverse direction connectivity register, a side chain first direction connectivity register, and a side chain second direction connectivity register. Therefore, the stereochemical data of the compounds can be described and stored in a three-dimensional manner. By using the above-mentioned registers, furthermore, the data stored in the main atom right direction connectivity register and those stored in the main atom reverse direction connectivity register can be exchanged for each of the fields of the same atom address numbers, and the data stored in the side chain first direction connectivity register and those stored in the side chain second direction connectivity register can be exchanged for each of the fields of the same atom address numbers. Accordingly, for a chain compound, the stored data can be changed from those of a formula to those of a formula which is turned by 180° in the plane of the paper. For a ring compound, the stored data can be changed from those of a formula to those of a formula that is turned back side front. Consequently, whether the formulas to be compared are identical or not can be easily discriminated. Furthermore, the present invention can be applied to the analysis of the systematic nomenclature of a compound including stereodescriptors for preparing an atom connection table. Here, the initial stereospecific input of a fundamental skeleton (such as pentane or cholestane) can be readily performed by the mere input of atom address numbers of the bonded atoms along the right direction or the reverse direction of the registers. According to the present invention, furthermore, the data system of stereospecific compounds can be established to exhibit very great effects for retrieving the compound data.

In the memory device according to the second and third embodiments of the present invention, provision is made of a bonded atom priority comparator circuit, an atom priority register, a bonded atom rotational direction discriminator circuit, first and second stereodescriptor reading circuits, and first and second side chain atom direction examining circuits. It is therefore possible to automatically and easily determine in which one of the side chain first direction connectivity register and the side chain second direction connectivity register the side-chain atoms should be stored in a three-dimensional manner.

In the memory device of the third embodiment of the present invention, the fundamental connection table register is provided with a condensation register, and the bonded atom priority comparator circuit discriminates the rotational direction based upon the data from the condensation register. Even for the compounds having condensed parts, therefore, the decision can be properly rendered concerning in which one of the side chain first direction connectivity register and the side chain second direction connectivity register the side-chain atoms should be stored three-dimensionally, or concerning whether the side-chain atoms should be left stored in the unknown direction connectivity register.

In the memory device accroding to the fourth embodiment of the present invention, provision is made of a first stereodescriptor examining circuit and a second stereodescriptor examining circuit subsequent to the bonded atom rotational direction discriminator circuit. Therefore, the stereodescriptors that are to be stored in the stereodescriptor register in the fundamental connection table register but that cannot be input from the graphic input register can be automatically and easily discriminated.

What is claimed is:

1. A method for storing stereochemical information about chemical compounds wherein:

atom address numbers are assigned to at least main atoms among the atoms constituting a compound;

atom address numbers of main atoms bonded to said main atoms in the right direction are stored to corespond to atom address numbers of the bonding main atoms in a main atom right direction connectivity register which describes the connectivity of the main atoms forming a skeleton of the compound in the right direction;

atom address numbers of main atoms bonded to said main atoms in the reverse direction are stored to correspond to atom address numbers of the bonding main atoms in a main atom reverse direction connectivity register which describes the connectivity of the main atoms forming a skeleton of the compound in the reverse direction;

atom address numbers or atomic symbols of side-chain atoms connected to the main atoms of said compound in the first direction, are stored in a side chain first direction connectivity register so as to correspond to atom address numbers of the bonding main atoms; and atom address numbers or atomic symbols of side-chain atoms connected to the main atoms of said compound in the second direction, are stored in a side chain second direction connectivity register so as to correspond to atom address numbers of the bonding main atoms.

2. A device for storing stereochemical information about chemical compounds, comprising:

(a) a fundamental connection table register which consists of:

an atom address number register that stores atom address numbers assigned to at least main atoms among the atoms constituting the compound;

a locant register that stores locants so as to correspond to atom address number of the atoms, said locants specifying the positions of at least main atoms among the atoms constituting said compound, from the chemical point of view;

an element register which stores the kinds of atoms to which said atom address numbers are assigned so as to correspond to the atom address numbers of the atoms;

a stereodescriptor register which stores the stereodescriptors assigned to asymmetric atoms in said compound so as to correspond to the atom address numbers of the asymmetric atoms;

a main atom right direction connectivity register which stores atom address numbers of main atoms bonded in the right direction to the main atoms forming a skeleton of said compound, so as to correspond to atom address numbers of the bonding main atoms;

a main atom reverse direction connectivity register which stores atom address numbers of main atoms bonded in the reverse direction to the main atoms which form a skeleton of said compound, so as to correspond to atom address numbers of the bonding main atoms;

a side chain first direction connectivity register which stores atom address numbers or atomic symbols of side-chain atoms bonded in the first direction to the main atoms of said compound, so as to correspond to atom address numbers of the bonding main atoms;

a side chain second direction connectivity register which stores atom address numbers or atomic symbols of side-chain atoms bonded in the second direction to the main atoms of said compound, so as to correspond to atom address numbers of the bonding main atoms; and an unknown direction connectivity register which stores atom address numbers of side-chain atoms that are to be stored either in said side chain first direction connectivity register or in said side chain second direction connectivity register, so as to correspond to atom address numbers of the bonding main atoms to which said side-chain atoms will be bonded;

(b) a systematic nomenclature input register which inputs the systematic nomenclature of a compound in the form of character data;

(c) a dictionary register which stores a variety of data of the compound;

(d) a fundamental connection table preparation circuit which processes the compound input to said systematic nomenclature input register based upon the data of said dictionary register, and which stores the required data in said atom address number register, in said locant register, in said element register, in said stereodescriptor register, in said main atom right direction connectivity register, in said main atom reverse direction connectivity register, and in said unknown direction connectivity register of said fundamental connection table register, so as to correspond to the atom address numbers;

(e) an atom priority register which sotres priorities in weight of the atoms that are bonded to asymmetric atoms of the compound;

(f) a bonded atom priority comparator circuit which gives priorities to the atoms bonded to the asymmetric atoms in the compound, based upon the signals from the predetermined registers storing the data among the registers of said fundamental connection table register and based upon the data from said atom priority register;

(g) a bonded atom rotational direction discriminator circuit which discriminates whether the rotational direction from the heavy atoms to the light atoms as determined by said bonded atom priority comparator circuit is in agreement with the clockwise rotational direction as viewed from the direction of an atom stored in the field of atom address number of said asymmetric atom in said main atom right direction connectivity register to an atom stored in the field of atom address number of said asymmetric atom in said main atom reverse direction connectivity register;

(h) a first stereodescriptor reading circuit which reads out stereodescriptors from the field of atom address number of said asymmetric atom in said stereodescriptor register, upon receipt of a coincidence signal produced by said bonded atom rotational direction discriminator circuit;

(i) a second stereodescriptor reading circuit which reads out stereodescriptors from the field of atom address number of said asymmetric atom in said stereodescriptor register, upon receipt of a non-coincidence signal produced by said bonded atom rotational direction discriminator circuit;

(j) a first side chain atom direction examining circuit which, when said first stereodescriptor reading circuit has read a stereodescriptor R upon receipt of a coincidence signal, stores the hydrogen atom or the lightest atom among a plurality of atoms stored in said unknown direction connectivity register in the field of atom address number of said asymmetric atom in said side chain second direction connectivity register, stores the other atom in said unknown direction connectivity register in the field of atom address number of said asymmetric atom in said side chain first direction connectivity register, and when said first stereodescriptor reading circuit has read a stereodescriptor S, stores the hydrogen atom or the lightest atom among a plurality of atoms stored in said unknown direction connectivity register in the field of atom address number of said asymmetric atom in said side chain first direction connectivity register, and stores the other atom in said unknown direction connectivity register in the field of atom address number of said asymmetric atom in said side chain second direction connectivity register; and (k) a second side chain atom direction examining circuit which, when said second stereodescriptor reading circuit has read a stereodescriptor R upon receipt of a non-coincidence signal, stores the hydrogen atom or the lightest atoms among a plurality of atoms stored in said unknown direction connectivity register in the field of atom address number of said asymmetric atom in said side chain first direction connectivity register, stores the other atom in said unknown direction connectivity register in the field of atom address number of said asymmetric atom in said side chain second direction connectivity register, and when said second stereodescriptor reading circuit has read a stereodescriptor S, stores the hydrogen atom or the lightest atom among a plurality of atoms stored in said unknown direction connectivity register in the field of atom address number of said asymmetric atom in said side chain second direction connectivity register, and stores the other atom in said unknown direction connectivity register in the field of atom address number of said asymmetric atom in said side chain first direction connectivity register.

3. A device for storing stereochemical information about chemical compounds, comprising, (a) a fundamental connection table register which consists of:

an atom address number register that stores atom address numbers assigned to at least main atoms among the atoms constituting the compound;

a locant register that stores locants so as to correspond to atom address numbers of the atoms, said locants specifying the positions of at least main atoms among the atoms constituting said compound, from the chemical point of view;

an element register which stores the kinds of atoms to which said atom address numbers are assigned so as to correspond to the atom address numbers of the atoms;

a condensation register for storing condensation symbols so as to correspond to atom address numbers of atoms which constitute a condensed part in said compound;

a stereodescriptor register which stores the stereodescriptors assigned to asymmetric atoms in said compound so as to correspond to the atom address numbers of the asymmetric atoms;

a main atom right direction connectivity register which stores atom address numbers of main atoms bonded in the right direction to the main atoms forming a skeleton of said compound, so as to correspond to atom address numbers of the bonding main atoms;

a main atom reverse direction connectivity register which stores atom address numbers of main atoms bonded in the reverse direction to the main atoms which form a skeleton of said compound, so as to correspond to atom address numbers of the bonding main atoms;

a side chain first direction connectivity register which stores atom address numbers or atomic symbols of side-chain atoms bonded in the first direction to the main atoms of said compound, so as to correspond to atom address numbers of the bonding main atoms;

a side chain second direction connectivity register which stores atom address numbers or atomic symbols of side-chain atoms bonded in the second direction to the main atoms of said compound, so as to correspond to atom address numbers of the bonding main atoms; and an unknown direction connectivity register which stores atom address numbers of side-chain atoms that are to be stored either in said side chain first direction connectivity register or in said side chain second direction connectivity register, so as to correspond to atom address numbers of the bonding main atoms to which said side-chain atoms will be bonded and which stores atom address numbers of atoms corresponding to atoms on one side in the condensed part so as to correspond to atom address numbers of the atoms of said one side;

(b) a systematic nomenclature input register which inputs the systematic nomenclature of a compound in the form of character data;

(c) a dictionary register which stores a variety of data of the compound;

(d) a fundamental connection table preparation circuit which processes the compound input to said systematic nomenclature input register based upon the data of said dictionary register, and which stores the required data in said atom address number register, in said locant register, in said element register, in said condensation register, in said stereodescriptor register, in said main atom right direction connectivity register, in said main atom reverse direction connectivity register, and in said unknown direction connectivity register of said fundamental connection table register, so as to correspond to the atom address numbers;

(e) an atom priority register which stores priorities in weight of the atoms that are bonded to asymmetric atoms of the compound;

(f) a bonded atom priority comparator circuit which gives priorities to the atoms bonded to the asymmetric atoms in the compound, based upon the signals from the predetermined registers storing the data among the registers of said fundamental connection table register and based upon the data from said atom priority register;

(g) a bonded atom rotational direction discriminator circuit which discriminates whether the rotational direction from the heavy atoms to the light atoms as determined by said bonded atom priority comparator circuit is in agreement with the clockwise rotational direction (counterclockwise direction in the condensed part) as viewed from the direction of an atom stored in the field of atom address number of said asymmetric atom in said main atom right direction connectivity register to an atom stored in the field of atom address number of said asymmetric atom in said main atom reverse direction connectivity register;

(h) a first stereodescriptor reading circuit which reads out stereodescriptors from the field of atom address number of said asymmetric atom in said stereodescriptor register, upon receipt of a coincidence signal produced by said bonded atom rotational direction discriminator circuit;

(i) a second stereodescriptor reading circuit which reads out stereodescriptors from the field of atom address number of said asymmetric atom in said stereodescriptor register, upon receipt of a non-coincidence signal produced by said bonded atom rotational direction discriminator circuit;

(j) a first side chain atom direction examining circuit which, when aid first stereodescriptor reading circuit has read a stereodescriptor R upon receipt of a coincidence signal, stores the hydrogen atom or the lightest atom among a plurality of atoms stored in said unknown direction connectivity register in the field of atom address number of said asymmetric atom in said side chain second direction connectivity register, stores the other atom in said unknown direction connectivity register in the field of atom address number of said asymmetric atom in said side chain first direction connectivity register, or maintains the other atom stored in the unknown direction connectivity register when it is the atom in the condensed part, and when said first stereodescriptor reading circuit has read a stereodescriptor S, stores the hydrogen atom or the lightest atom among a plurality of atoms stored in said unknown direction connectivity register in the field of atom address number of said asymmetric atom in said side chain first direction connectivity register, and stores the other atom in said unknown direction connectivity register in the field of atom address number of said asymmetric atom in said side chain second direction connectivity register, or maintains the other atom stored in the unknown direction connectivity register when it is the atom in the condensed part; and (k) a second side chain atom direction examining circuit which, when said second stereodescriptor reading circuit has read a stereodescriptor R upon receipt of a non-coincidence signal, stores the hydrogen atom or the lightest atoms among a plurality of atoms stored in said unknown direction connectivity register in the field of atom address number of said asymmetric atom in said side chain first direction connectivity register, stores the other atom in said unknown direction connectivity register in the field of atom address number of said asymmetric atom in said side chain second direction connectivity register, or maintains the other atom stored in the unknown direction connectivity register when it is the atom in the condensed part, and when said second stereodescriptor reading circuit has read a stereodescriptor S, stores the hydrogen atom or the lightest atom among a plurality of atoms stored in said unknown direction connectivity register in the field of atom address number of said asymmetric atom in said side chain second direction connectivity register, and stores the other atom in said unknown direction connectivity register in the field of atom address number of said asymmetric atom in said side chain first direction connectivity register, or maintains the other atom stored in the unknown direction connectivity register when it is the atom in the condensed part.

4. A device for storing stereochemical information about chemical compounds, comprising:

(a) a fundamental connection table register which consists of:

an atom address number register that stores atom address numbers assigned to at least main atoms among the atoms constituting the compound;

a locant register that stores locants so as to correspond to atom address numbers of the atoms, said locants specifying the positions of at least main atoms among the atoms constituting said compound, from the chemical point of view;

an element register which stores the kinds of atoms to which said atom address numbers are assigned so as to correspond to the atom address numbers of the atoms;

a condensation register for storing condensation symbols so as to correspond to atom address numbers of atoms which constitute a condensed part in said compound;

a stereodescriptor register which stores the stereodescriptors assigned to asymmetric atoms in said compound so as to correspond to the atom address numbers of the asymmetric atoms;

a main atom right direction connectivity register which stores atom address numbes of main atoms bonded in the right direction to the main atoms forming a skeleton of said compound, so as to correspond to atom address numbers of the bonding main atoms;

a main atom reverse direction connectivity register which stores atom address numbers of main atoms bonded in the reverse direction to the main atoms which form a skeleton of said compound, so as to correspond to atom address numbers of the bonding main atoms;

a side chain first direction connectivity register which stores atom address numbers or atomic symbols of side-chain atoms bonded in the first direction to the main atoms of said compound, so as to correspond to atom address numbes of the bonding main atoms;

a side chain second direction connectivity register which stores atom address numbers or atomic symbols of side-chain atoms bonded in the second direction to the main atoms of said compound, so as to correspond to atom address numbers of the bonding main atoms; and an unknown direction connectivity register which stores atom address numbers of main atoms that will be bonded to main atoms on one side in the condensed part in said compound so as to correspond to atom address numbers of the main atoms of said one side;

(b) a graphic input register which works to store required data of atoms to which atom address numbers are assigned in the compound that is expressed in the form of a graph, in said atom address number register, in said element register, in said condensation register, in said main atom right direction connectivity register, in said main atom reverse direction connectivity register, in said side chain first direction connectivity register, in said side chain second direction connectivity register, and in said unknown direction connectivity register of said fundamental connection table register, so as to correspond to atom address numbers of the bonding atoms;

(c) an atom priority register which stores priorities in weight of the atoms that are connected to asymmetric atoms of the compound;

(d) a bonded atom priority comparator circuit which gives priorities to the atoms bonded to the asymmetric atoms in the compound, based upon the signals from the predetermined registers storing the data among the registers of said fundamental connection table register and based upon the data from said atom priority register;

(e) a bonded atom rotational direction discriminator circuit which discriminates whether the rotational direction from the heavy atoms to the light atoms as determined by said bonded atom priority comparator circuit is in agreement with the clockwise rotational direction (counterclockwise direction in the condensed part) as viewed from the direction of an atom stored in the field of atom address number of said asymmetric atom in said main atom right direction connectivity register to an atom stored in the field of atom address number of said asymmetric atom in said main atom reverse direction connectivity register;

(f) a first stereodescriptor examining circuit which, upon receipt of a signal from said bonded atom rotational direction discriminator circuit indicating that the rotational directions are in agreement with regard to atoms bonded to an asymmetric atom of a given atom address number, works to compare the weight of atoms bonded to the asymmetric atom stored in said registers so as to correspond to atom address numbers of the asymmetric atoms, and when a light atom has been stored in the side chain second direction connectivity register and said asymmetric atom is not present in the condensed part, works to store the stereodescriptor R in said stereodescriptor register, or works to store the stereodescriptor S in said stereodescriptor register when said asymmetric atom is present in the condensed part, and when a light atom has been stored in said side chain first direction connectivity register and said asymmetric atom is not present in the condensed part, works to store the stereodescriptor S in said stereodescriptor register, or works to store the stereodescriptor R in said stereodescriptor register when said asymmetric atom is present in the condensed part; and (g) a second stereodescriptor examining circuit, which upon receipt of a signal from said bonded atom rotational discriminator circuit indicating that the rotational directions are in agreement with regard to atoms bonded to an asymmetric atom of a given atom address number, works to compare the weight of atoms bonded to the asymmetric atom stored in said registers so as to correspond to atom address numbers of the asymmetric atoms, and when a light atom has been stored in said side chain second direction connectivity register and said asymmetric atom is not present in the condensed part, works to store the stereodescriptor S in said stereodescriptor register, or works to store the stereodescriptor R in said stereodescriptor register when said asymmetric atom is present in the condensed part, and when a light atom has been stored in said side chain first direction connectivity register and said asymmetric atom is not present in the condensed part, works to store the stereodescriptor R in said stereodescriptor register, or works to store the stereodescriptor S in said stereodescriptor register when said asymmetric atom is present in the condensed part.

* * * * *